US010874717B2

(12) United States Patent
Brody

(10) Patent No.: US 10,874,717 B2
(45) Date of Patent: Dec. 29, 2020

(54) PEGYLATED GROWTH HORMONE ANTAGONISTS

(71) Applicant: Burr Oak Therapeutics LLC, Columbus, OH (US)

(72) Inventor: Richard S. Brody, Columbus, OH (US)

( * ) Notice: Subject to any disclaimer, the term of this patent is extended or adjusted under 35 U.S.C. 154(b) by 58 days.

(21) Appl. No.: 16/216,230

(22) Filed: Dec. 11, 2018

(65) Prior Publication Data

US 2019/0099497 A1 Apr. 4, 2019

Related U.S. Application Data

(63) Continuation-in-part of application No. 15/204,425, filed on Jul. 7, 2016, now abandoned.

(60) Provisional application No. 62/189,525, filed on Jul. 7, 2015.

(51) Int. Cl.
*A61K 38/27* (2006.01)
*A61K 47/60* (2017.01)
*C07K 14/61* (2006.01)

(52) U.S. Cl.
CPC .............. *A61K 38/27* (2013.01); *A61K 47/60* (2017.08); *C07K 14/61* (2013.01)

(58) Field of Classification Search
None
See application file for complete search history.

(56) References Cited

U.S. PATENT DOCUMENTS 7,399,839 B2 7/2008 Cox
8,778,880 B2 7/2014 Cho et al.
8,957,023 B2 2/2015 Cox
2014/0163204 A1 6/2014 Cox

OTHER PUBLICATIONS

Khanal et al. (Chemistry 23(60): 15133-15142, 2017).*
Alconcel, Steevens NS, Arnold S. Baas, and Heather D. Maynard. “FDA-approved poly (ethylene glycol)-protein conjugate drugs.” Polymer Chemistry 2.7 (2011): 1442-1448.
Bell, Sheila M., et al. “R-spondin 2 is required for normal laryngeal-tracheal, lung and limb morphogenesis.” Development 135 (2008): 1049-1058.
Chapman, Andrew P. “PEGylated antibodies and antibody fragments for improved therapy: a review.” Advanced drug delivery reviews 54.4 (2002): 531-545.
Chen, Youhai, et al. “Regulatory T cell clones induced by oral tolerance: suppression of autoimmune encephalomyelitis.” Science 265.5176 (1994): 1237-1240.
Cho, Hong Y., et al. “Synthesis of biocompatible PEG-based star polymers with cationic and degradable core for siRNA delivery.” Biomacromolecules 12.10 (2011): 3478-3486.
Dehouck, Yves, et al. “Fast and accurate predictions of protein stability changes upon mutations using statistical potentials and neural networks: PoPMuSiC-2.0.” Bioinformatics 25.19 (2009): 2537-2543.
Dehouck, Yves, et al. “PoPMuSiC 2.1: a web server for the estimation of protein stability changes upon mutation and sequence optimality,” BMC bioinformatics 12.1 (2011) 151.
Ding, Qiurong, et al. “Enhanced efficiency of human pluripotent stem cell genome editing through replacing TALENs with CRISPRs.” Cell stem cell 12.4 (2013): 393-394.
Doherty, Daniel H., et al. “Site-specific PEGylation of engineered cysteine analogues of recombinant human granulocyte-macrophage colony-stimulating factor.” Bioconjugate chemistry 16.5 (2005): 1291-1298.
Fam, Christine M., et al. “PEGylation improves the pharmacokinetic properties and ability of interferon gamma to inhibit growth of a human tumor xenograft in athymic mice.” Journal of Interferon & Cytokine Research 34.10 (2014): 759-768.
Finn, Robert D., et al. “The Pfam protein families database.” Nucleic acids research 38. suppl_1 (2009): D211-D222.
Da Silva Freitas, Débora, Anna Mero, and Gianfranco Pasut. “Chemical and enzymatic site specific PEGylation of hGH.” Bioconjugate chemistry 24.3 (2013): 456-463.
Guex, Nicolas, and Manuel C. Peitsch. “SWISS-MODEL and the Swiss-Pdb Viewer: an environment for comparative protein modeling,” electrophoresis 18.15 (1997): 2714-2723.
http://babylone.ulb.ac.be/popmusic.
Kling, Mitchel A., et al. “Vascular disease and dementias: paradigm shifts to drive research in new directions.” Alzheimer’s & Dementia 9.1 (2013): 76-92.
Lee, Jaeseon, et al. “Interferon gamma suppresses collagen-induced arthritis by regulation of Th17 through the induction of indoleamine-2, 3-deoxygenase.” PloS one 8.4 (2013): e60900.
Lee, Kang Choon, et al. “Isolation, characterization, and stability of positional isomers of mono-PEGylated salmon calcitonins.” Pharmaceutical research 16.6 (1999): 813-818.
Li, Shyh-Dar, and Leaf Huang. “Stealth nanoparticles: high density but sheddable PEG is a key for tumor targeting.” Journal of controlled release: official journal of the Controlled Release Society 145.3 (2010): 178.
Parveen, Suphiya, and Sanjeeb K. Sahoo. “Nanomedicine.” Clinical pharmacokinetics 45.10 (2006): 965-988.
Pasut, Gianfranco, and Francesco M. Veronese. “State of the art in PEGylation: the great versatility achieved after forty years of research.” Journal of controlled release 161.2 (2012): 461-472.
Povoski, Stephen P., and Hooman Khabiri. “Persistent left superior vena cava: review of the literature, clinical implications, and relevance of alterations in thoracic central venous anatomy as pertaining to the general principles of central venous access device placement and venography in cancer patients.” World journal of surgical oncology 9.1 (2011): 173.

(Continued)

*Primary Examiner* — Christine J Saoud

(57) ABSTRACT

A composition that is a human growth hormone receptor antagonist comprising human growth hormone receptor antagonist G120K, wherein one or two amino acids of human growth hormone receptor antagonist G120K have been mutated to cysteine; and a polyethylene glycol molecule conjugated to each substituted cysteine in the human growth hormone receptor antagonist G120K mutant.

4 Claims, No Drawings

Specification includes a Sequence Listing.

(56) References Cited

OTHER PUBLICATIONS

Povoski, Stephen P., et al. "Single molecular weight discrete PEG compounds: emerging roles in molecular diagnostics, imaging and therapeutics." Expert review of molecular diagnostics 13.4 (2013): 315-319.

Qiu, Huawei, et al. "Site-specific PEGylation of human thyroid stimulating hormone to prolong duration of action." Bioconjugate chemistry 24.3 (2013): 408-418.

Rasmussen, Michael Højby, et al. "Pegylated long-acting human growth hormone is well-tolerated in healthy subjects and possesses a potential once-weekly pharmacokinetic and pharmacodynamic treatment profile." The Journal of Clinical Endocrinology & Metabolism 95.7 (2010): 3411-3417.

Rosendahl, Mary S., et al. "A long-acting, highly potent interferon α-2 conjugate created using site-specific PEGylation." Bioconjugate chemistry 16.1 (2005): 200-207.

Ross, R. J. M., et al. "Binding and functional studies with the growth hormone receptor antagonist, B2036-PEG (pegvisomant), reveal effects of pegylation and evidence that it binds to a receptor dimer." The Journal of Clinical Endocrinology & Metabolism 86.4 (2001): 1716-1723.

Sundström, Michael, et al. "Crystal structure of an antagonist mutant of human growth hormone, G120R, in complex with its receptor at 2.9 Å resolution." Journal of Biological Chemistry 271.50 (1996): 32197-32203.

Van der Lely, A. J., and John J. Kopchick. "Growth hormone receptor antagonists." Neuroendocrinology 83.3-4 (2006): 264-268.

Wu, Guoyao. "Functional amino acids in nutrition and health." (2013): 407-411.

Zhang, Xiaoyong, et al. "PEGylation and polyPEGylation of nanodiamond." Polymer 53.15 (2012): 3178-3184.

* cited by examiner

PEGYLATED GROWTH HORMONE ANTAGONISTS

CROSS-REFERENCE TO RELATED APPLICATIONS

This patent application is a continuation-in-part of U.S. patent application Ser. No. 15/204,425 filed on Jul. 7, 2016 and entitled "Pegylated Growth Hormone Antagonists", which claimed the benefit of U.S. Provisional Patent Application Ser. No. 62/189,525 filed on Jul. 7, 2015 and entitled "Pegylated Growth Hormone Antagonists", the disclosures of which are hereby incorporated by reference herein in their entirety and made part of the present U.S. utility patent application for all purposes.

REFERENCE TO A SEQUENCE LISTING

A sequence listing in computer readable form (CRF) is on file. The sequence listing is in an ASCII text (.txt) file entitled SEQIDNOS_1_24_ST25.txt created on Dec. 10, 2018 and is 33 KB in size. The sequence listing is incorporated by reference as if fully recited herein.

BACKGROUND OF THE INVENTION

The described invention relates in general to compositions for use as receptor antagonists, and more specifically to novel human growth hormone antagonists that have the potential to be highly effective therapeutics.

Human growth hormone, also known as somatotropin or somatropin, is a peptide hormone that stimulates growth, cell reproduction, and regeneration in humans and other animals. Growth hormone is a type of mitogen that is specific only to certain kinds of cells and is a 191-amino acid, single-chain polypeptide that is synthesized, stored, and secreted by somatotropic cells within the lateral wings of the anterior pituitary gland. Acromegaly is a syndrome that results when the anterior pituitary gland produces excess growth hormone (hGH) after epiphyseal plate closure at puberty. If hGH is produced in excess prior to epiphyseal plate closure, the result is gigantism (or giantism). A number of disorders may increase the pituitary's hGH output, although most commonly it involves a tumor called pituitary adenoma, derived from a distinct type of cell (somatotrophs). Acromegaly most commonly affects adults in middle age and can result in severe disfigurement, complicating conditions, and premature death if untreated. Because of its pathogenesis and slow progression, the disease is hard to diagnose in the early stages and is frequently missed for years until changes in external features, especially of the face, become noticeable.

A receptor is a protein molecule usually found embedded within the plasma membrane surface of a cell that receives chemical signals from outside the cell. When such chemical signals bind to a receptor, they cause some form of cellular/tissue response such as, for example, a change in the electrical activity of the cell. In this sense, a receptor is a protein molecule that recognizes and responds to endogenous chemical signals. An agonist, such as human growth hormone, is a chemical composition that binds to a receptor and activates the receptor to produce a biological response. Whereas an agonist causes an action, an antagonist blocks the action of the agonist and an inverse agonist causes an action opposite to that of the agonist. A receptor antagonist is a type of receptor ligand or drug that blocks or dampens agonist-mediated responses rather than provoking a biological response itself upon binding to a receptor. These compositions are sometimes called blockers and examples include alpha blockers, beta blockers, and calcium channel blockers. In pharmacology, antagonists have affinity but no efficacy for their cognate receptors, and binding will disrupt the interaction and inhibit the function of an agonist or inverse agonist at receptors. Antagonists mediate their effects by binding to the active (orthosteric) site or to other (allosteric) sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists achieve their potency by competing with endogenous ligands or substrates at structurally defined binding sites on receptors. By definition, antagonists display no efficacy to activate the receptors they bind and antagonists do not maintain the ability to activate a receptor. Once bound, however, antagonists inhibit the function of agonists, inverse agonists, and partial agonists.

Growth hormone receptor antagonists such as the product pegvisomant (sold under the trademark SOMAVERT®) are used in the treatment of acromegaly. Such compositions are used if the tumor of the pituitary gland causing the acromegaly cannot be controlled with surgery or radiation and the use of somatostatin analogues is unsuccessful. Pegvisomant is typically delivered as a powder that is mixed with water and injected under the skin.

PEGylation is the process of both covalent and non-covalent amalgamation of polyethylene glycol (PEG) polymer chains to molecules and macrostructures, such as drugs, peptides, antibody fragments, or therapeutic proteins. PEGylation is routinely achieved by incubation of a reactive derivative of PEG with the target molecule and produces alterations in physiochemical properties, including changes in molecular size and molecular charge. These physical and chemical changes increase systemic retention of the therapeutic agent and can influence the binding affinity of the therapeutic moiety to the cell receptors and can alter the absorption and distribution patterns. The covalent attachment of PEG to a drug or therapeutic protein can also "mask" the agent from the host's immune system (i.e., reducing immunogenicity and antigenicity), and increase the hydrodynamic size (i.e., size in solution) of the agent which prolongs its circulatory time by reducing renal clearance. PEGylation can also provide water solubility to hydrophobic drugs and proteins.

PEGylation, by increasing the molecular weight of a molecule, can impart several significant pharmacological advantages over the unmodified form of the molecule, such as: (i) improved drug solubility; (ii) reduced dosage frequency, without diminished efficacy and with potentially reduced toxicity; (iii) extended circulating life; (iv) increased drug stability; and (v) enhanced protection from proteolytic degradation. PEGylated drugs also include the following commercial advantages: (i) opportunities for new delivery formats and dosing regimens; and (ii) extended patent life of previously approved drugs. PEG is a particularly attractive polymer for conjugation and the specific characteristics of PEG moieties relevant to pharmaceutical applications include: (i) water solubility; (ii) high mobility in solution; (iii) lack of toxicity and low immunogenicity; and (v) altered distribution in the body.

The addition of high molecular weight polyethylene glycols (PEGs) to proteins has been previously shown to increase the in-vivo half-lives of these proteins by a size dependent decrease in elimination by the kidneys. The addition of PEGs also lowers the immunogenicity of the proteins and decreases aggregation and protease cleavage (Pasut and Vronese, 2012; and Parveen and Sahoo, 2006). Multiple known PEGylated proteins have been approved by the USFDA for therapeutic use, including hormones, cytokines, antibody fragments, and enzymes (Pasut, and Veronese, 2012; Alconcel et al., 2011; and Kling, 2013). Thus, there is an ongoing need for the further development of PEGylated therapeutics, particularly for use in the treatment of diseases that are responsive to the use of human growth hormone (hGH) receptor antagonists or other receptor antagonists.

SUMMARY OF THE INVENTION

The following provides a summary of certain exemplary embodiments of the present invention. This summary is not an extensive overview and is not intended to identify key or critical aspects or elements of the present invention or to delineate its scope. However, it is to be understood that the use of indefinite articles in the language used to describe and claim the present invention is not intended in any way to limit the described system. Rather the use of “a” or “an” should be interpreted to mean “at least one” or “one or more”. As will be appreciated by one skilled in the art, the single letter amino acid abbreviations used herein follow the IUPAC format.

In accordance with one aspect of the present invention, a first composition or compound that functions as a human growth hormone receptor antagonist is provided. This human growth hormone receptor antagonist includes human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is selected from the group consisting of N99, T142, and H151, and wherein the two amino acids mutated to cysteine are selected from the group consisting of N99/T142, N99/H151, and T142/H151; and a polyethylene glycol molecule conjugated to each substituted cysteine in the human growth hormone receptor antagonist G120K mutant.

In accordance with another aspect of the present invention, a second composition or compound that functions as a human growth hormone receptor antagonist is provided. This human growth hormone receptor antagonist includes human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is selected from the group consisting of N99, T142, and H151, and wherein the two amino acids mutated to cysteine are selected from the group consisting of N99/T142, N99/H151, and T142/H151; and a polyethylene glycol molecule conjugated to each substituted cysteine in the human growth hormone receptor antagonist G120K mutant, wherein the polyethylene glycol molecule conjugated to the one amino acid mutated to cysteine is a polydispersed 40 kDa branched polyethylene glycol molecule; and wherein the polyethylene glycol molecules conjugated to the two amino acids mutated to cysteine are either two 40 kDa branched polyethylene glycol molecules or two 4.5 kDa branched polyethylene glycols each containing three carboxylate anions.

In yet another aspect of this invention, a third composition or compound that functions as a human growth hormone receptor antagonist is provided. This human growth hormone receptor antagonist includes human growth hormone receptor antagonist G120K, wherein two amino acids of human growth hormone receptor antagonist G120K have been mutated to cysteine, and wherein the two amino acids mutated to cysteine are selected from the group consisting of N99/T142, N99/H151, and T142/H151; and a polyethylene glycol molecule conjugated to each substituted cysteine in the human growth hormone receptor antagonist G120K mutant.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention.

DETAILED DESCRIPTION OF THE INVENTION

Exemplary embodiments of the present invention are described below. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides novel human growth hormone (hGH) antagonists for use primarily as therapeutics. The hGH antagonists of this invention are typically made by mutating one or more selected amino acids of hGH G120K, a known hGH antagonist, to cysteines and then conjugating the cysteines to chemically activated polyethylene glycol molecules. The positions of the substituted cysteines have been selected for minimal loss in receptor binding activity after conjugation with polyethylene glycol. The specific type and number of polyethylene glycol modifiers of this invention have been selected to produce antagonists with increased in-vivo half-lives.

Two important variables in the preparation of PEGylated proteins in accordance with this invention are: (i) the amino acid position used for PEG attachment; and (ii) the size and type of the conjugated PEG. Initial research with similar compositions was done using random attachment of relatively small PEGs (e.g., about 5 kDa) to multiple lysines on the surfaces of proteins. This procedure successfully increased the in vivo half-lives of the proteins, but resulted in large decreases in the affinity of the proteins for their receptors. More recent experimental approaches have added PEG molecules to specific amino acid sites on proteins. Two common methods used for site specific PEGylation are: (i) addition of PEG to the N-terminal amine of proteins by way of low pH reductive amination; and (ii) addition of PEG to the thiol groups of cysteines that are either native to the protein or engineered into specific positions. Other methods include PEG addition to unnatural amino acids; PEG addition to proteins C-termini by way of intein fusion proteins; and PEG addition to accessible glutamines by way of transaminase catalysis (Pasut and Veronese, 2012).

Two or more different types of polyethylene glycol (PEG) molecules are utilized with the present invention. A first type of PEG is prepared by polymerization and is by nature polydispersed, in that there is a distribution of molecular weight products around the average molecular weight. A second class of polyethylene glycols are discrete PEGs (dPEG®s; Quanta BioDesign). Such dPEG®s are single PEG molecules that are prepared by step-wise, organic chemistry so that each dPEG® species is a pure single compound with a specific structure and molecular weight (Povosky et al., 2013). The different types of PEGs have been produced as both linear and branched structures. For large polydispersed PEGs, the addition of a branched PEG to a protein may cause less of a decrease in binding affinity and a greater increase in half-life than addition of a linear PEG of the same molecular weight (Zhang et al., 2012). Branched dPEG®s have been shown to increase protein half-lives and a negatively charged dPEG® has been shown to be particularly efficacious (Ding et al., 2013).

Pegylated Growth Hormone Antagonists

The conversion of hGH from a growth agonist to a growth antagonist requires only a single amino acid change at hGH position 120 from the native glycine to any amino acid except alanine (Chen et al., 1994). This molecule, however, cannot be used as a therapeutic for conditions of excess growth (e.g., acromegaly) due to its short in vivo half-life. Researchers have addressed this problem by the addition of polyethylene glycol molecules to the hGH antagonist hGH G120K to decrease the clearance of the molecule through the kidneys. SOMAVERT® (pegvisomant), an FDA approved treatment for acromegaly, contains 4-6 linear PEG molecules with molecular weights of 5000 Daltons each. The addition of the PEGs, which are attached randomly to surface lysines (van der Lely and Kopchick, 2006), increases the in vivo half-life of the antagonist from less than an hour to approximately 72 hours (Finn, 2009). The affinity of the pegylated antagonist for the membrane bound receptor, however, is reduced approximately 30 fold compared with the unpegylated molecule (Ross et al., 2001). Despite the decrease in receptor affinity, SOMAVERT® (pegvisomant) is an effective treatment for acromegaly, although a large daily dose of 5-30 mg is typically prescribed.

The loss of receptor binding that occurs after the addition of multiple low molecular weight PEGs (about 5 kDa) to random lysines on a protein was common with early protein-PEG conjugates (Parveen and Sahoo, 2006). More recently, however, researchers have made conjugates with higher receptor binding activity by adding a single higher molecular weight PEG to specific amino acid positions on the protein target (Pasut and Veronese, 2012). In the case of growth hormone antagonists, either a 20 kDa or a 40 kDa linear PEG was added to the N-terminus of the unpegylated precursor to SOMAVERT® (B2036) (pegvisomant) using reductive alkylation at a low pH (Wu et al., 2013). The addition of the 20 kDa PEG and the 40 kDa PEG reduced the affinity of the antagonist for the soluble hGH receptor by about 50% and about 95%, respectively. The ability of these molecules to inhibit the production of insulin growth factor-1 (IGF-1) in rats was tested. While the 40 kDa PEG conjugate was inactive, the 20 kDa conjugate reduced the IGF-1 production by 30 to 40%.

Pegylated Growth Hormone

Insights regarding the predicted effects of different PEGylation strategies on growth hormone antagonist activity and half-life can be obtained by analysis of the results from PEGylation of human growth hormone (hGH) (Finn, 2009). Cox and coworkers (2007) mutated the threonine at position 3 of human growth hormone to cysteine (T3C hGH) and then conjugated the cysteine to a 20 kDa linear PEG. The activity of hGH, measured by a proliferation assay, decreased by about 4 fold and the half-life increased by about 8 fold. Similar increases in half-life occurred after the enzyme catalyzed addition of a 20 kDa PEG to Gln141 and the chemical addition of a 20 kDa PEG to the N-terminus (Freitas et al., 2013). The addition of a 30 kDa linear PEG to different amino acid positions, which were mutated to chemically active non-native amino acids, resulted, in the optimal cases, in a roughly 10 fold loss of proliferation activity and a roughly 10 fold increase in half-life (Cho et al., 2011). The addition of a linear 43 kDa PEG to position 141 (Gln mutated to cysteine) was reported to increase the half-life ~30 fold and the addition of a branched 40 kDa PEG to the N-terminus of hGH was reported to increase the half-life about 20 fold (Rasmussen et al., 2010).

PEGylated Cytokines

The site-specific addition of PEGs to cytokines, which have molecular weights similar to that of hGH, indicates that a single PEG can cause a significant increase in half-life. Rosendahl et al. (2005) reported that addition of a 10 kDa PEG, a 20 kDa PEG, and a 40 kDa PEG to position 5 of Interferon $\alpha$-2, after mutation of this position to cysteine, reduced the in vitro bioactivity by a factor of 2-3. In contrast, the half-life increased for the 10 kDa, 20 kDa PEG, and 40 kDa PEG by factors of 14, 23 and 40 respectively. A similar result was found for the addition of different molecular weight PEGs to human granulocyte-macrophage colony-stimulating factor (Doherty et al., 2005). Bell et al. (2008) found that the addition of either a 20 kDa or a 40 kDa PEG to position 111 (M111C) of interferon $\alpha$ led to a three-fold decrease in receptor binding activity. The half-lives for the 20 kDa and the 40 kDa substituted interferons increased by 25 fold and 39 fold respectively. In contrast, the site specific addition of a 40 kDa PEG to interferon $\beta$-1b only increased the half-life of by about three-fold (Lee et al., 2013).

Qiu et al. (2013) substituted position 22 of human thyroid stimulating hormone with a linear 40 kDa PEG, a two branched 40 kDa PEG, and a three branched 40 kDa PEG and found that the receptor binding activity decreased by 5 fold, 14 fold, and 11 fold respectively. A comparison of the half-lives of these different conjugates was not reported. Fam et al. (2014) studied the effect of the addition of 10 kDa, 20 kDa, and 40 kDa PEGs to position 103 of interferon $\gamma$ and found that the PEGs did not significantly affect the cytokine's in vitro activity, but in all cases the half-life was increased by about 30 fold.

Antibody Fragments

Extensive work has been done on the addition of PEGs to antibody fragments to increase their residence time in the body. Lee et al. (1999) conjugated a single chain antibody fragment (scFv MAb; 26 kDa) with six different PEG polymers with MWs ranging from 2 to 20 kDa. These conjugates showed longer half-lives compared to their non-PEGylated parent. Increasing PEG polymer length was found to be more effective for half-life extension than increasing total PEG mass. Li et. al. (2010) showed that the addition of two discrete linear PEG units conjugated to random lysines on a diabody resulted in longer blood retention times than unpegylated or polydisperse pegylated products. Chapman et al. (2002) demonstrated that the half-lives of antibody Fab' fragments (about 50 kDa) are directly related to the size and numbers of site-directed PEGs.

Lee et al. (2013) found that an increase in linear, randomly conjugated PEG mass (4-20 kDa) in scFv-PEG conjugates effectively increased half-lives roughly linearly with mass. These workers found that a single 20 kDa PEG was more effective than four 5,000 PEGs, concluding that PEG length was more important than PEG mass. In a study of the roughly 50 kDa Fab' antibody fragment, the site specific addition of a 4.4 kDa branched discrete PEG (dPEG) increased the half-life by a factor of about two over unconjugated Fab' (Ding et al., 2013).

Selection of Amino Acid Positions of hGH G120K to Mutate to Cysteine

In various embodiments of the present invention, PEGylated versions of the antagonist hGH G120K were prepared by attaching PEGs to cysteine residues that have been incorporated into the antagonist sequence through genetic engineering. The antagonist positions selected for mutation to cysteine were selected using the X-ray structure of the complex of hGH with an hGH receptor dimer ($hGHR_2$; Sundstrom et al., 1996). The structure of hGH when bound to $hGHR_2$ is almost identical to the structure of the hGH antagonist hGH G120R when the antagonist is bound to the same receptor (Sundstrom et al., 1996).

Two criteria, based on the hGH-$hGHR_2$ crystal structure, were used to select amino acids for cysteine mutation: (i) accessibility of the amino acid to solvent; and (ii) making the substitution of cysteine for the selected amino acid needs close to an energetically neutral process. The solvent accessibility of each amino acid in hGH-$hGHR_2$ was determined by way of the modeling programs Swiss PDB Viewer (Guex and Peitsch, 1997) and PoPMuSIC (Dehouck et al., 2009; Dehouck et al., 2011). The energetic cost of substituting cysteine for each amino acid position was determined using the *Prediction of Protein Mutant Stability Changes* (PoPMuSIC) program (http://babylone.ulb.ac.be/popmusic/).

The amino acids selected by solvent (e.g., water) accessibility and mutation energy considerations are listed below in Table 1 under "All Selected Positions" in seven spatially separate domains. However, being accessible to water is not necessarily a sole criteria for selection; the amino acids need to be accessible to the much larger PEG molecules in order for the PEGylated antagonists to bind to a target receptor. The X-ray structure of hGH-$hGHR_2$ was inspected to determine if the side chains of the selected amino acids are directed towards solvent or towards the hGH-$hGHR_2$ protein complex. Amino acid positions whose side chains point into the solvent are the most desirable candidates for PEG substitution and are listed below in Table 1 under "Final Selection". An additional position, H151, was also selected for cysteine mutation. This position is part of a section of Loop 3 that was not apparent in the crystal structure. The general location of the missing segment is pointing away from the hGH-$hGHR_2$ protein complex.

TABLE 1

Final Selection of Amino Acid Positions

| | All Selected Positions | Final Selection (amino acids whose side chains point away from the protein structure) |
|---|---|---|
| Domain 1 (N-Terminus): | F1, T3 | T3 |
| Domain 2 (Loop 1): | E39 | E39 |
| Domain 3 (Loop 1): | P48 | P48 |
| Domain 4 (Loop 1): | Q69 | Q69 |
| Domain 5 (Loop 2): | N99, L101 | N99, L101 |
| Domain 6 (Loop 3): | T142, D147, D154 | T142 |
| Domain 7 (C-Terminus) | G190 | G190 |

Selection of PEGs for Conjugation to hGH G120K Mutants

Two different classes of polyethylene glycol (PEG) molecules are utilized with the present invention. The first class of PEGs was prepared by polymerization and has been used to modify proteins in order to increase their in vivo half-lives (Kling, 2013). This type of PEG is by nature polydispersed, meaning that there is a distribution of molecular weight products around the average molecular weight. The PEGs include a 20 kDa linear PEG (Layson Bio, MPEG-MAL-20,000), a 40 kDa branched PEG (NOF, Sunbright GL2-400MA), and a linear 40 kDa PEG (NOF, Sunbright ME-400MA). These PEGS each contain a maleimide group for conjugation to the free sulfhydryl groups of the mutant proteins. The second class of polyethylene glycols are "discrete" PEGs (dPEG®s; Quanta BioDesign). These dPEG®s are pure single PEG molecules that are prepared using step-wise, organic chemistry so that each dPEG® species is a pure single compound with a specific structure and molecular weight (Povosky et al., 2013). The dPEGs used in this invention, which typically contain a maleimide group for coupling to free thiols, include the following: a tri-branched molecule with a molecular weight of 4473 Daltons and a carboxylate anion at the terminus of each branch (Quanta BioDesign #10451, MAL-dPEGA); a neutral tri-branched molecule with a molecular weight of 4299 Daltons (Quanta BioDesign #4229, MAL-dPEGB); a neutral 9-branched molecule with a molecular weight of 8324 (Quanta Biodesign #10484; MAL-dPEGE); and a neutral 9-branched molecule with a molecular weight of 15,592 (Quanta Biodesign #11487; MAL-dPEGF). The tri-branched 4473 Da molecule has been conjugated to an antibody fragment and its effect on blood clearance in mice has been investigated (Ding et al., 2013). While the added dPEG® increased the molecular weight of a 50 kDa protein molecular weight by only about 8%, the "area under the curve" (AUC) for blood clearance increased by a factor of about 2.5 over the AUC for the unPEGylated protein.

Purification and Pegylation of hGH G120K Mutants

Cell Disruption

A cell pellet obtained from centrifugation of 250 mL of growth medium containing the expressed mutant was suspended in 10 mL PBS and combined with 0.05 mL of a protease inhibitor cocktail without EDTA (Sigma P8849). The solution was cooled in an ice water mixture and sonicated for four minutes in 30 second bursts. After each sonication, the sample was cooled in the ice-water mixture until the temperature was below 4° C. The sonicated suspension was then centrifuged at 4° C. and 25,000×g for 30 minutes and the supernatant was collected and kept on ice.

Affinity Purification

The sonicated supernatant was adjusted to 0.3 M sodium chloride and made 5 mM imidazole by addition of a pH 7 solution of 150 mM imidazole. The sample was then applied to a gravity flow column having a stoppered outlet packed with 5 mL of TALON® (Clontech) immobilized metal affinity resin (IMAC). The resin was equilibrated in 0.05 M sodium phosphate buffer, pH 7.0 containing 5 mM imidazole and 0.3 M sodium chloride prior to addition of the supernatant. The top of the column was then also stoppered and the column mixed end-over-end at room temperature for 30 minutes. The column was then allowed to drain and washed with at least five 5 mL aliquots of equilibration buffer. Washing was continued until the A(280) nm of the eluent no longer decreased. The column was then eluted with pH 7 equilibration buffer containing 150 mM imidazole and the product containing fractions were made 5 mM EDTA by addition of a 100 mM solution of disodium EDTA adjusted to pH 7.

TEV Protease Cleavage of His-Tag

The IMAC purified mutant was concentrated by molecular filtration to 2 mg/mL and 0.5 mL of the solution was combined with 0.05 mL of a solution containing 15 mM reduced glutathione+1.5 mM oxidized glutathione. An aliquot of 0.04 mg TEV Protease (TurboTev, Accelagen) was then added and the solution incubated for two hours at room temperature followed by overnight incubation at 4° C. The imidazole containing buffer was then exchanged on a spin column for a buffer containing 0.05 M sodium phosphate, pH 7.0 and 0.3 M sodium chloride.

Pegylation and Purification

The desalted mutant was PEGylated by making the solution 0.5 mM maleimide-PEG and incubating the reaction for two hours at room temperature followed by overnight incubation at 4° C. The PEGylated mutant was then applied to a gravity flow IMAC column containing 1 mL TALON® resin equilibrated in the spin column buffer and the column was washed with 5 CVs of the same buffer. The TALON® flow through and wash contained the product, which was then concentrated by a centrifugal concentrator to 0.3 mL and purified by size exclusion chromatography on a Superdex 200 Increase 10/300 GL column (GE Healthcare) equilibrated in 0.05 M Tris Buffer, pH 8, containing 0.15 M sodium chloride and 10% glycerol. The product fractions were combined and analyzed for protein concentration by absorption at A(280) nm and for purity by SDS-PAGE. The addition of a single dPEGB to the single cysteine mutants and two dPEGBs to the double cysteine mutants was confirmed by MALDI mass spectrometry.

Competition ELISA Assay of Relative Affinity for the hGH Receptor

A Competition ELISA required the preparation of biotinylated hGH, which was prepared by standard methods (Hermanson, 2008) using Biotin-dPEG12-NHS (Quanta BioDesign). Microtiter plates (Corning 96 well plates, half-area, polystyrene) were coated with 0.05 mL of 0.125 μg/mL solutions of the hGH receptor (R&D Systems, 1210-GR-50; cloned as a chimira with an antibody Fc region) in a 0.05 M sodium carbonate buffer at pH 9.6 and incubated either at 37° C. for one hour or overnight at 4° C. After washing the plate three times, with three minute incubations between washes, with of 0.125 mL PBS, 0.05% Tween 20 (Wash Buffer), the plates were blocked for one hour by incubation with 2% BSA in PBS.

Preliminary ELISA assays were performed to determine the concentration of biotin-hGH to use in the completion ELISA. Plates coated with the hGH receptor and blocked were incubated for one hour at RT with different concentrations of biotinylated hGH dissolved in PBS, 0.1% BSA, 0.05% Tween 20 (Dilution Buffer). The plates were then washed 3× with Wash Buffer and incubated for 1 hour at room temperature with 0.5 ug/mL Streptavidin-HRP (Pierce, 21130) in Dilution Buffer. The plates were again washed 3 times and developed by the addition of 0.05 mL TMB (KPL). After incubation for 2-20 minutes at room temperature, the plates were then quenched by the addition of 0.1 mL 1 M HCl and read on a plate reader at 450 nm.

A concentration of biotin-hGH was selected such that the assay response was in the linear range of the plot of biotin-hGH versus A(450) nm (approximately 1 OD unit). Competition assays were performed by the preparation of solutions in polypropylene 96 well plates that contained the selected concentration of biotin-hGH and varying concentrations of hGH, hGH G120K mutant, or pegylated hGH G120K mutant. Ninety-six well immunoassay plates were coated with the hHG receptor, blocked as described above, and then incubated for 1 hour at RT with the solutions containing the selected concentration of biotin-hGH and different concentrations of the inhibitors. The plates were then washed and treated with Streptavidin-HRP and TMB as described above.

The concentration of recombinant hGH that gave a 50% inhibition of the assay response ($IC_{50}$) was used as the standard to determine the relative affinities of the mutants for the hGH receptor. Each assay plate contained a series of concentrations of both the hGH standard and the mutants to be tested and the relative $IC_{50}$ values were determined. Two polydispersed PEGs (ME400MA and GL2-400MA) were conjugated to the free thiols of hGH G120K-H151C and hGH G120K-N99C. G120K-H151C-ME400MA and Gl20K-H151C-GL2-400MA had, respectively, 20% and 50% of the inhibitory activity of G120K. N99C-ME400MA and N99C-GL2-400MA had 20% and 2% of the inhibitory activity of G120K.

The pegylated hGH antagonist hGH G120K-T142C-GL2-400MA was been prepared and purified using the procedures described herein. GL2-400MA is a 40 kDa two-branched PEG containing a maleimide group that was reacted with the inserted cysteine of hGH G120K-T142C. This molecule, which is expected to have a long serum half-life (see Zhang et al., 2012), retained 50% of the hGH receptor binding activity of unmodified hGH. The molecule hGH G120K-H151C-GL2-400MA, which is also disclosed herein, was shown to also retain 50% of the hGH receptor binding activity of unmodified hGH.

The binding affinities of the different dPEG® conjugated mutants of the present invention relative to that of hGH are shown in Table 2, below. Seven single mutants and three double mutants were conjugated to a single tri-branched molecule dPEG® with a molecular weight of 4473 Daltons (dPEGA) and the molecule was purified as described. As shown in Table 2, certain of these single mutants were also conjugated to three other dPEGs. Three double cysteine mutants were also prepared and conjugated to different dPEGs, as shown in Table 2.

TABLE 2

Receptor Binding Activity of hGH 120K Mutants[1]

| hGH Mutant - All Mutants Contain the G120K Mutation | Percent Receptor Binding Activities Relative to that of hGH Determined from the Concentration of Each Sample that Yields 50% Inhibition ($I_{50}$) | | | |
|---|---|---|---|---|
| dPEG Substitution | dPEGA[2] | dPEGB[2] | dPEGE[2] | dPEGF[2] |
| G120K-T3C-dPEGX | 70 | 70 | NT | NT |
| G120K-E39C-dPEGX | 20 | NT | NT | NT |
| G120K-P48C-dPEGX | 20 | NT | NT | NT |
| G120K-Q69C-dPEGX | 20 | NT | NT | NT |
| G120K-N99C-dPEGX | 90 | 70 | 40 | 4 |
| G120K-T142C-dPEGX | 50 | 90 | 50 | 20 |
| G120K-H151C-dPEGX | 100 | 60 | 40 | 4 |
| G120K-N99C-dPEGX-H151C-dPEGX | 20 | 40 | 20 | —[3] |
| G120K-T142C-dPEGX-N99C-dPEGX | 50 | 80 | 30 | —[3] |
| G120K-T142C-dPEGX-H151C-dPEGX | 50 | 40 | 10 | —[3] |

[1]The receptor binding activities were determined using a competitive ELISA where the recombinant receptor was bound to a plate and the concentration of each sample needed to inhibit the binding of biotin-hGH to the coated plate by 50% (I50) was determined. The Table entries show the $I_{50}$s relative to that of hGH, which is defined as 100%, and are rounded to a single significant figure. Only a single competitive ELISA was run for most of the mutants and the estimated relative standard deviation is 25%. Entries marked NT were not tested in this assay.

[2]dPEGA is a tri-branched molecule with a molecular weight of 4473 Daltons and a carboxylate anion at the terminus of each branch; dPEGB is a neutral tri-branched molecule with a molecular weight of 4299 Daltons, dPEGE is a neutral 9-branched molecule with a molecular weight of 8324; and dPEGF is a neutral 9-branched molecule with a molecular weight of 15,592.

[3]These reactions did not proceed to the double PEGylated product.

Western Blot Assay for the Ability of PEGylated Mutants to Inhibit the Stimulation of STAT 5 Phosphorylation by hGH The ability of the PEGylated mutants of the present invention to inhibit the stimulation of Stat5 Protein phosphorylation by hGH was measured in a cell-based assay. IM9 cells were incubated in RPMI media for two hours. The cells were then resuspended in fresh RPMI media at 1 million cells per mL and treated with either hGH, pegylated hGH mutants, or hGH+pegylated mutants at concentrations from 0 to 5000 ng/mL. The treated cells were then incubated for 15 minutes at 37° C. in a 5% carbon dioxide incubator. The cells were then spun down, lysed in a buffer containing 1% Triton X-100 and sodium orthovanadate, and loaded on an SDS PAGE gel. The gel was run under standard conditions and the proteins then transferred electrophoretically to a PVDF membrane. The membrane was blocked and then incubated overnight at 4° C. with a mixture of rabbit anti-Stat5 Protein antibody and rabbit anti-β-actin antibody (positive cell control). The membrane was then washed and incubated with a HRP conjugated goat anti-rabbit antibody for one hour at room temperature. Finally, the bands were visualized using Pierce Supersignal West chemiluminescent substrate. Qualitative results for the PEGylated mutants are given in Table 3, below. The relative abilities of the hGH G120K pegylated double mutants of the present invention to inhibit stimulation of STAT 5 phosphorylation by hGH as measured by Western blot assay are presented in Table 4, below.

TABLE 3

Western Blot Assay for the Ability of the PEGylated Mutants to Inhibit the Stimulation of STAT 5 Phosphorylation by hGH[1]

| hGH Mutant - All Mutants Contain the G120K Mutation | Ability of the Pegylated Mutants to Inhibit the Stimulation of STAT 5 Phosphorylation by hGH | | | |
|---|---|---|---|---|
| dPEG Substitution | dPEGA[2] | dPEGB[2] | dPEGE[2] | dPEGF[2] |
| G120K-T3C-dPEGX | NT | + | NT | NT |
| G120K-E39C-dPEGX | NT | NT | NT | NT |
| G120K-P48C-dPEGX | NT | NT | NT | NT |
| G120K-Q69C-dPEGX | NT | NT | NT | NT |
| G120K-N99C-dPEGX | + | + | NT | NT |
| G120K-T142C-dPEGX | + | + | + | + |
| G120K-H151C-dPEGX | + | + | NT | NT |
| G120K-N99C-dPEGX-H151C-dPEGX | + | + | NT | NT |
| G120K-T142C-dPEGX-N99C-dPEGX | + | + | + | NT |
| G120K-T142C-dPEGX-H151C-dPEGX | NT | + | + | NT |

[1]The Western assay qualitatively measures the abilities of hGH antagonists to inhibit the hGH stimulation of STAT 5 phosphorylation. The inhibition is expressed as relative to the inhibition obtained with the parent antagonist hGH G120K. In all cases, the relative abilities of the pegylated antagonists to inhibit STAT 5 phosphorylation was between ~20% and ~100% that of hGH G120K. The variation between duplicate runs was too great to make this a quantitative assay. Entries marked NT were not tested in this assay.

[2]dPEGA is a tri-branched molecule with a molecular weight of 4473 Daltons and a carboxylate anion at the terminus of each branch; dPEGB is a neutral tri-branched molecule with a molecular weight of 4299 Daltons, dPEGE is a neutral 9-branched molecule with a molecular weight of 8324; and dPEGF is a neutral 9-branched molecule with a molecular weight of 15,592.

TABLE 4

Western blot assay for the Ability of the hGH G120K PEGylated Double Mutants to Inhibit the Stimulation of STAT 5 Phosphorylation by hGH[3]

| hGH G120K Mutant - All Mutants Contain the G120K Mutation | Percent Inhibition of Stimulation of STAT 5 Phosphorylation by hGH[3] |
|---|---|
| G120K-N99C-dPEGA-H151C-dPEGA[4] | 20% |
| G120K-T142C-dPEGA-N99C-dPEGA[4] | 20% |
| G120K-T142C-dPEGA-H151C-dPEGA[4] | 50% |

[3]This Western Blot assay measures the abilities of pegylated hGH antagonists to inhibit the hGH stimulation of STAT 5 phosphorylation. The inhibition is expressed as relative to the inhibition obtained with the parent antagonist hGH G120K. The quantification was obtained from the intensities of the phosphorylated STAT 5 band on the Western Blots.

[4]dPEGA is a tri-branched molecule with a molecular weight of 4473 Daltons and a carboxylate anion at the terminus of each branch.

As indicated by the disclosure above, the compositions of the present invention provide novel human growth hormone receptor antagonists that are useful in therapeutic applications. For reference purposes, SEQ ID NO: 1 provides the DNA sequence for human growth hormone WThGH and SEQ ID NO: 2 and provides the amino acid sequence for human growth hormone WThGH (mature form). Human growth hormone receptor antagonist G120K is the parent receptor antagonist for the compositions of the present invention, and for reference purposes, SEQ ID NO: 3 provides the DNA sequence for human growth hormone receptor antagonist G120K and SEQ ID NO: 4 provides the amino acid sequence for human growth hormone receptor antagonist G120K (mature form). As previously stated, the single letter amino acid abbreviations used herein follow the IUPAC format.

A first human growth hormone antagonist in accordance with an exemplary embodiment of the present invention includes human growth hormone antagonist G120K, wherein amino acid T3 has been mutated to cysteine, and wherein a polyethylene glycol molecule has been conjugated to the cysteine mutation. SEQ ID NO: 5 provides the DNA sequence for human growth hormone antagonist G120K-T3C and SEQ ID NO: 6 provides the amino acid for sequence human growth hormone antagonist G120K-T3C.

A second human growth hormone antagonist in accordance with an exemplary embodiment of the present invention includes human growth hormone antagonist G120K, wherein amino acid E39 has been mutated to cysteine, and wherein a polyethylene glycol molecule has been conjugated to the cysteine mutation. SEQ ID NO: 7 provides the DNA sequence for human growth hormone antagonist G120K-E39C and SEQ ID NO: 8 provides the amino acid sequence for human growth hormone antagonist G120K-E39C.

A third human growth hormone antagonist in accordance with an exemplary embodiment of the present invention includes human growth hormone antagonist G120K, wherein amino acid P48 has been mutated to cysteine, and wherein a polyethylene glycol molecule has been conjugated to the cysteine mutation. SEQ ID NO: 9 provides the DNA sequence for human growth hormone antagonist G120K-P48C and SEQ ID NO: 10 provides the amino acid sequence for human growth hormone antagonist G120K-P48C.

A fourth human growth hormone antagonist in accordance with an exemplary embodiment of the present invention includes human growth hormone antagonist G120K, wherein amino acid Q69 has been mutated to cysteine, and wherein a polyethylene glycol molecule has been conjugated to the cysteine mutation. SEQ ID NO: 11 provides the DNA sequence for human growth hormone antagonist G120K-

Q69C and SEQ ID NO: 12 provides the amino acid sequence for human growth hormone antagonist G120K-Q69C.

A fifth human growth hormone antagonist in accordance with an exemplary embodiment of the present invention includes human growth hormone antagonist G120K, wherein amino acid N99 has been mutated to cysteine, and wherein a polyethylene glycol molecule has been conjugated to the cysteine mutation. SEQ ID NO: 13 provides the DNA sequence for human growth hormone antagonist G120K-N99C and SEQ ID NO: 14 provides the amino acid sequence for human growth hormone antagonist G120K-N99C.

A sixth human growth hormone antagonist in accordance with an exemplary embodiment of the present invention includes human growth hormone antagonist G120K, wherein amino acid T142 has been mutated to cysteine, and wherein a polyethylene glycol molecule has been conjugated to the cysteine mutation. SEQ ID NO: 15 provides the DNA sequence for human growth hormone antagonist G120K-T142C and SEQ ID NO: 16 provides the amino acid sequence for human growth hormone antagonist G120K-T142C.

A seventh human growth hormone antagonist in accordance with an exemplary embodiment of the present invention includes human growth hormone antagonist G120K, wherein amino acid H151 has been mutated to cysteine, and wherein a polyethylene glycol molecule has been conjugated to the cysteine mutation. SEQ ID NO: 17 provides the DNA sequence for human growth hormone antagonist G120K-H151C and SEQ ID NO: 18 provides the amino acid sequence for human growth hormone antagonist G120K-H151C.

An eighth human growth hormone antagonist in accordance with an exemplary embodiment of the present invention includes human growth hormone antagonist G120K, wherein amino acids N99 and H151 have been mutated to cysteine, and wherein a polyethylene glycol molecule has been conjugated to each cysteine mutation. SEQ ID NO: 19 provides the DNA sequence for human growth hormone antagonist G120K-N99C-dPEGX-H151C and SEQ ID NO: 20 provides the amino acid sequence for human growth hormone antagonist G120K-N99C-dPEGX-H151C.

A ninth human growth hormone antagonist in accordance with an exemplary embodiment of the present invention includes human growth hormone antagonist G120K, wherein amino acids T142 and N99 have been mutated to cysteine, and wherein a polyethylene glycol molecule has been conjugated to each cysteine mutation. SEQ ID NO: 21 provides the DNA sequence for human growth hormone antagonist G120K-T142C-dPEGX-N99C and SEQ ID NO: 22 provides the amino acid sequence for human growth hormone antagonist G120K-T142C-dPEGX-N99C.

A tenth human growth hormone antagonist in accordance with an exemplary embodiment of the present invention includes human growth hormone antagonist G120K, wherein amino acids T142 and H151 have been mutated to cysteine, and wherein a polyethylene glycol molecule has been conjugated to each cysteine mutation. SEQ ID NO: 23 provides the DNA sequence for human growth hormone antagonist G120K-T142C-dPEGX-H151C and SEQ ID NO: 24 provides the amino acid sequence for human growth hormone antagonist G120K-T142C-dPEGX-H151C.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

What is claimed:

1. A human growth hormone receptor antagonist, comprising:

(a) human growth hormone receptor antagonist G120K having a DNA sequence of SEQ ID NO: 3 and an amino acid sequence of SEQ ID NO: 4, wherein two amino acids of human growth hormone receptor antagonist G120K have been mutated to cysteine, wherein the two amino acids mutated to cysteine are T142 and H151; and (b) a polyethylene glycol molecule conjugated to each substituted cysteine in the human growth hormone receptor antagonist G120K mutant, wherein the polyethylene glycol molecules conjugated to the two amino acids mutated to cysteine are two 4.5 kDa branched polyethylene glycols each containing three carboxylate anions, wherein the polyethylene glycol molecule is prepared by step-wise organic chemistry and is a substantially pure single compound, and wherein the polyethylene glycol molecule is a branched structure.

2. The composition of claim 1, wherein the polyethylene glycol molecule contains a maleimide group for conjugation to a free sulfhydryl group.

3. The composition of claim 1, wherein the human growth hormone receptor antagonist is encoded by a DNA molecule having the sequence consisting of SEQ ID NO:23, and wherein the human growth hormone receptor antagonist has the amino acid sequence consisting of SEQ ID NO:24.

4. A method for inhibiting human growth hormone activity in a subject in need thereof comprising administering the composition of claim 1.

* * * * *

SEQUENCE LISTING

```
<160> NUMBER OF SEQ ID NOS: 24

<210> SEQ ID NO 1
<211> LENGTH: 567
<212> TYPE: DNA
<213> ORGANISM: Artificial Sequence
<220> FEATURE:
<223> OTHER INFORMATION: WThGH (DNA) Human Growth Hormone

<400> SEQUENCE: 1

ttcccaacca ttcccttatc caggcttttt gacaacgcta tgctccgcgc catcgtctgc      60

accagctggc ctttgacacc taccaggagt ttgaagaagc ctatatccca aggaacagaa     120

gtattcattc ctgcagaacc cccagacctc cctctgtttc tcagagtcat tccgacaccc     180

tccaacaggg aggaaacaca acagaaatcc aacctagagc tgctccgatc tccctgctgc     240

tcatccagtc gtggctggag cccgtgcagt tcctcaggag tgtcttgcca acagcctggt     300

gtacggcgcc tctgacagca acgtctatga cctcctaaag gacctgagga aggcatccaa     360

acgctgatgg ggaggctgga agatggcagc ccccggactg ggcaatcttc aagcagacct     420

acagcaagtt cgacacaaac tcacacaacg atgacgcact actaagaact acgggctgct     480

ctactgcttc aggaaggaca tggacaaggt cgagacattc ctcgcatcgt gcagtgccgc     540

tctgtggagg gcagctgtgg cttctag                                         567
```

-continued

<210> SEQ ID NO 2
<211> LENGTH: 188
<212> TYPE: PRT
<213> ORGANISM: Artificial Sequence
<220> FEATURE:
<223> OTHER INFORMATION: WThGH (amino acid) Human Growth Hormone (Mature Form)

<400> SEQUENCE: 2

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Leu Cys Phe Ser Glu Ser Ile Pro Thr Pro Ser Asn Arg Glu
    50                  55                  60

Glu Thr Gln Gln Lys Ser Asn Leu Glu Leu Leu Arg Ile Ser Leu Leu
65                  70                  75                  80

Leu Ile Gln Ser Trp Leu Glu Pro Val Gln Phe Leu Arg Ser Val Phe
                85                  90                  95

Ala Asn Ser Leu Val Tyr Gly Ala Ser Asp Ser Asn Val Asp Leu Leu
            100                 105                 110

Lys Asp Leu Glu Glu Gly Ile Gln Thr Leu Met Gly Arg Leu Glu Asp
        115                 120                 125

Gly Ser Pro Arg Thr Gly Gln Ile Phe Lys Gln Thr Tyr Ser Lys Phe
    130                 135                 140

Asp Thr Asn Ser His Asn Asp Asp Ala Leu Leu Lys Asn Tyr Gly Leu
145                 150                 155                 160

Leu Tyr Cys Phe Arg Lys Asp Met Lys Val Glu Thr Phe Leu Arg Ile
                165                 170                 175

Val Gln Cys Arg Ser Val Glu Gly Ser Cys Gly Phe
            180                 185
```

<210> SEQ ID NO 3
<211> LENGTH: 567
<212> TYPE: DNA
<213> ORGANISM: Artificial Sequence
<220> FEATURE:
<223> OTHER INFORMATION: G120K (DNA) Human Growth Hormone Antagonist G120K

<400> SEQUENCE: 3

```
ttcccaacca ttcccttatc caggcttttt gacaacgcta tgctccgcgc catcgtctgc     60

accagctggc ctttgacacc taccaggagt ttgaagaagc ctatatccca aggaacagaa    120

gtattcattc ctgcagaacc cccagacctc cctctgtttc tcagagtcat tccgacaccc    180

tccaacaggg aggaaacaca acagaaatcc aacctagagc tgctccgatc tccctgctgc    240

tcatccagtc gtggctggag cccgtgcagt tcctcaggag tgtcttgcca acagcctggt    300

gtacggcgcc tctgacagca acgtctatga cctcctaaag gacctgagga aaagatccaa    360

acgctgatgg ggaggctgga agatggcagc ccccggactg ggcaatcttc aagcagacct    420

acagcaagtt cgacacaaac tcacacaacg atgacgcact actaagaact acgggctgct    480

ctactgcttc aggaaggaca tggacaaggt cgagacattc ctcgcatcgt gcagtgccgc    540

tctgtggagg gcagctgtgg cttctag                                        567
```

-continued

<210> SEQ ID NO 4
<211> LENGTH: 188
<212> TYPE: PRT
<213> ORGANISM: Artificial Sequence
<220> FEATURE:
<223> OTHER INFORMATION: G120K (amino acid) Human Growth Hormone Antagonist G120K (Mature Form)

<400> SEQUENCE: 4

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Leu Cys Phe Ser Glu Ser Ile Pro Thr Pro Ser Asn Arg Glu
    50                  55                  60

Glu Thr Gln Gln Lys Ser Asn Leu Glu Leu Leu Arg Ile Ser Leu Leu
65                  70                  75                  80

Leu Ile Gln Ser Trp Leu Glu Pro Val Gln Phe Leu Arg Ser Val Phe
                85                  90                  95

Ala Asn Ser Leu Val Tyr Gly Ala Ser Asp Ser Asn Val Asp Leu Leu
            100                 105                 110

Lys Asp Leu Glu Glu Lys Ile Gln Thr Leu Met Gly Arg Leu Glu Asp
        115                 120                 125

Gly Ser Pro Arg Thr Gly Gln Ile Phe Lys Gln Thr Tyr Ser Lys Phe
    130                 135                 140

Asp Thr Asn Ser His Asn Asp Asp Ala Leu Leu Lys Asn Tyr Gly Leu
145                 150                 155                 160

Leu Tyr Cys Phe Arg Lys Asp Met Lys Val Glu Thr Phe Leu Arg Ile
                165                 170                 175

Val Gln Cys Arg Ser Val Glu Gly Ser Cys Gly Phe
            180                 185

<210> SEQ ID NO 5
<211> LENGTH: 645
<212> TYPE: DNA
<213> ORGANISM: Artificial Sequence
<220> FEATURE:
<223> OTHER INFORMATION: G120K-T3C (DNA) Synthetic Constructs / Mutant Human Growth Hormone Antagonist

<400> SEQUENCE: 5
atggcgcatc accaccacca tcacggcagc agcggcgaga acctgtactt ccagggtgga 60
agctcgggat tcccatgcat tcccttatcc aggctttttg acaacgctat gctccgcgcc 120
catcgtctgc accagctggc ctttgacacc taccaggagt ttgaagaagc ctatatccca 180
aaggaacaga agtattcatt cctgcagaac ccccagacct ccctctgttt ctcagagtct 240
attccgacac cctccaacag ggaggaaaca caacagaaat ccaacctaga gctgctccgc 300
atctccctgc tgctcatcca gtcgtggctg gagcccgtgc agttcctcag gagtgtcttc 360
gccaacagcc tggtgtacgg cgcctctgac agcaacgtct atgacctcct aaaggaccta 420
gaggaaaaga tccaaacgct gatggggagg ctggaagatg gcagcccccg gactgggcag 480
atcttcaagc agacctacag caagttcgac acaaactcac acaacgatga cgcactactc 540
aagaactacg ggctgctcta ctgcttcagg aaggacatgg acaaggtcga gacattcctg 600
cgcatcgtgc agtgccgctc tgtggagggc agctgtggct tctag 645

-continued

<210> SEQ ID NO 6
<211> LENGTH: 214
<212> TYPE: PRT
<213> ORGANISM: Artificial Sequence
<220> FEATURE:
<223> OTHER INFORMATION: G120K-T3C (amino acid) Synthetic Constructs / Mutant Human Growth Hormone Antagonists

<400> SEQUENCE: 6

```
Met Ala His His His His His His Gly Ser Ser Gly Glu Asn Leu Tyr
1               5                   10                  15

Phe Gln Gly Gly Ser Ser Gly Phe Pro Cys Ile Pro Leu Ser Arg Leu
            20                  25                  30

Phe Asp Asn Ala Met Leu Arg Ala His Arg Leu His Gln Leu Ala Phe
        35                  40                  45

Asp Thr Tyr Gln Glu Phe Glu Glu Ala Tyr Ile Pro Lys Glu Gln Lys
    50                  55                  60

Tyr Ser Phe Leu Gln Asn Pro Gln Thr Ser Leu Cys Phe Ser Glu Ser
65                  70                  75                  80

Ile Pro Thr Pro Ser Asn Arg Glu Glu Thr Gln Gln Lys Ser Asn Leu
                85                  90                  95

Glu Leu Leu Arg Ile Ser Leu Leu Leu Ile Gln Ser Trp Leu Glu Pro
            100                 105                 110

Val Gln Phe Leu Arg Ser Val Phe Ala Asn Ser Leu Val Tyr Gly Ala
        115                 120                 125

Ser Asp Ser Asn Val Tyr Asp Leu Leu Lys Asp Leu Glu Glu Lys Ile
    130                 135                 140

Gln Thr Leu Met Gly Arg Leu Glu Asp Gly Ser Pro Arg Thr Gly Gln
145                 150                 155                 160

Ile Phe Lys Gln Thr Tyr Ser Lys Phe Asp Thr Asn Ser His Asn Asp
                165                 170                 175

Asp Ala Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210
```

<210> SEQ ID NO 7
<211> LENGTH: 645
<212> TYPE: DNA
<213> ORGANISM: Artificial Sequence
<220> FEATURE:
<223> OTHER INFORMATION: G120K-E39C (DNA) Synthetic Constructs / Mutant Human Growth Hormone Antagnonist

<400> SEQUENCE: 7

```
atggcgcatc accaccacca tcacggcagc agcggcgaga acctgtactt ccagggtgga     60

agctcgggat tcccaaccat tcccttatcc aggctttttg acaacgctat gctccgcgcc    120

catcgtctgc accagctggc ctttgacacc taccaggagt ttgaagaagc ctatatccca    180

aagtgccaga agtattcatt cctgcagaac ccccagacct ccctctgttt ctcagagtct    240

attccgacac cctccaacag ggaggaaaca caacagaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480
```

atcttcaagc agacctacag caagttcgac acaaactcac acaacgatga cgcactactc 540
aagaactacg ggctgctcta ctgcttcagg aaggacatgg acaaggtcga gacattcctg 600
cgcatcgtgc agtgccgctc tgtggagggc agctgtggct tctag 645

<210> SEQ ID NO 8
<211> LENGTH: 214
<212> TYPE: PRT
<213> ORGANISM: Artificial Sequence
<220> FEATURE:
<223> OTHER INFORMATION: G120K-E39C (amino acid) Synthetic Constructs / Mutant Human Growth Hormone Antagonists

<400> SEQUENCE: 8

Met Ala His His His His His His Gly Ser Ser Gly Glu Asn Leu Tyr
1 5 10 15

Phe Gln Gly Gly Ser Ser Gly Phe Pro Thr Ile Pro Leu Ser Arg Leu
20 25 30

Phe Asp Asn Ala Met Leu Arg Ala His Arg Leu His Gln Leu Ala Phe
35 40 45

Asp Thr Tyr Gln Glu Phe Glu Glu Ala Tyr Ile Pro Lys Cys Gln Lys
50 55 60

Tyr Ser Phe Leu Gln Asn Pro Gln Thr Ser Leu Cys Phe Ser Glu Ser
65 70 75 80

Ile Pro Thr Pro Ser Asn Arg Glu Glu Thr Gln Gln Lys Ser Asn Leu
85 90 95

Glu Leu Leu Arg Ile Ser Leu Leu Leu Ile Gln Ser Trp Leu Glu Pro
100 105 110

Val Gln Phe Leu Arg Ser Val Phe Ala Asn Ser Leu Val Tyr Gly Ala
115 120 125

Ser Asp Ser Asn Val Tyr Asp Leu Leu Lys Asp Leu Glu Glu Lys Ile
130 135 140

Gln Thr Leu Met Gly Arg Leu Glu Asp Gly Ser Pro Arg Thr Gly Gln
145 150 155 160

Ile Phe Lys Gln Thr Tyr Ser Lys Phe Asp Thr Asn Ser His Asn Asp
165 170 175

Asp Ala Leu Leu Lys Asn Tyr Gly Leu Leu Tyr Cys Phe Arg Lys Asp
180 185 190

Met Asp Lys Val Glu Thr Phe Leu Arg Ile Val Gln Cys Arg Ser Val
195 200 205

Glu Gly Ser Cys Gly Phe
210

<210> SEQ ID NO 9
<211> LENGTH: 645
<212> TYPE: DNA
<213> ORGANISM: Artificial Sequence
<220> FEATURE:
<223> OTHER INFORMATION: G120K-P48C (DNA) Synthetic Constructs / Mutant Human Growth Hormone Antagonists

<400> SEQUENCE: 9
atggcgcatc accaccacca tcacggcagc agcggcgaga acctgtactt ccagggtgga 60
agctcgggat tcccaaccat tcccttatcc aggcttttg acaacgctat gctccgcgcc 120
catcgtctgc accagctggc ctttgacacc taccaggagt ttgaagaagc ctatatccca 180
aaggaacaga agtattcatt cctgcagaac tgtcagacct ccctctgttt ctcagagtct 240

```
attccgacac cctccaacag ggaggaaaca caacagaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480

atcttcaagc agacctacag caagttcgac acaaactcac acaacgatga cgcactactc    540

aagaactacg ggctgctcta ctgcttcagg aaggacatgg acaaggtcga gacattcctg    600

cgcatcgtgc agtgccgctc tgtggagggc agctgtggct tctag                    645


<210> SEQ ID NO 10
<211> LENGTH: 70
<212> TYPE: PRT
<213> ORGANISM: Artificial Sequence
<220> FEATURE:
<223> OTHER INFORMATION: G120K-P48C (amino acid) Synthetic Constructs /
      Mutant Human Growth Hormone Antagonists

<400> SEQUENCE: 10

Gln Thr Leu Met Gly Arg Leu Glu Asp Gly Ser Pro Arg Thr Gly Gln
1               5                   10                  15

Ile Phe Lys Gln Thr Tyr Ser Lys Phe Asp Thr Asn Ser His Asn Asp
            20                  25                  30

Asp Ala Leu Leu Lys Asn Tyr Gly Leu Leu Tyr Cys Phe Arg Lys Asp
        35                  40                  45

Met Asp Lys Val Glu Thr Phe Leu Arg Ile Val Gln Cys Arg Ser Val
    50                  55                  60

Glu Gly Ser Cys Gly Phe
65                  70


<210> SEQ ID NO 11
<211> LENGTH: 645
<212> TYPE: DNA
<213> ORGANISM: Artificial Sequence
<220> FEATURE:
<223> OTHER INFORMATION: G120K-Q69C (DNA) Synthetic Constructs / Mutant
      Human Growth Hormone Antagonists

<400> SEQUENCE: 11

atggcgcatc accaccacca tcacggcagc agcggcgaga acctgtactt ccagggtgga     60

agctcgggat tcccaaccat tcccttatcc aggctttttg acaacgctat gctccgcgcc    120

catcgtctgc accagctggc ctttgacacc taccaggagt ttgaagaagc ctatatccca    180

aaggaacaga agtattcatt cctgcagaac ccccagacct ccctctgttt ctcagagtct    240

attccgacac cctccaacag ggaggaaaca cagtgcaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480

atcttcaagc agacctacag caagttcgac acaaactcac acaacgatga cgcactactc    540

aagaactacg ggctgctcta ctgcttcagg aaggacatgg acaaggtcga gacattcctg    600

cgcatcgtgc agtgccgctc tgtggagggc agctgtggct tctag                    645


<210> SEQ ID NO 12
<211> LENGTH: 214
<212> TYPE: PRT
<213> ORGANISM: Artificial Sequence
<220> FEATURE:
```

<223> OTHER INFORMATION: G120K-Q69C (amino acid) Synthetic Constructs / Mutant Human Growth Hormone Antagonists

<400> SEQUENCE: 12

```
Met Ala His His His His His His Gly Ser Ser Gly Glu Asn Leu Tyr
1               5                   10                  15

Phe Gln Gly Gly Ser Ser Gly Phe Pro Thr Ile Pro Leu Ser Arg Leu
            20                  25                  30

Phe Asp Asn Ala Met Leu Arg Ala His Arg Leu His Gln Leu Ala Phe
        35                  40                  45

Asp Thr Tyr Gln Glu Phe Glu Glu Ala Tyr Ile Pro Lys Glu Gln Lys
    50                  55                  60

Tyr Ser Phe Leu Gln Asn Pro Gln Thr Ser Leu Cys Phe Ser Glu Ser
65                  70                  75                  80

Ile Pro Thr Pro Ser Asn Arg Glu Glu Thr Gln Cys Lys Ser Asn Leu
                85                  90                  95

Glu Leu Leu Arg Ile Ser Leu Leu Leu Ile Gln Ser Trp Leu Glu Pro
            100                 105                 110

Val Gln Phe Leu Arg Ser Val Phe Ala Asn Ser Leu Val Tyr Gly Ala
        115                 120                 125

Ser Asp Ser Asn Val Tyr Asp Leu Leu Lys Asp Leu Glu Glu Lys Ile
    130                 135                 140

Gln Thr Leu Met Gly Arg Leu Glu Asp Gly Ser Pro Arg Thr Gly Gln
145                 150                 155                 160

Ile Phe Lys Gln Thr Tyr Ser Lys Phe Asp Thr Asn Ser His Asn Asp
                165                 170                 175

Asp Ala Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210
```

<210> SEQ ID NO 13
<211> LENGTH: 576
<212> TYPE: DNA
<213> ORGANISM: Artificial Sequence
<220> FEATURE:
<223> OTHER INFORMATION: G120K-N99C (DNA) Synthetic Constructs / Mutant Human Growth Hormone Antagonists

<400> SEQUENCE: 13

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagacctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

-continued

<210> SEQ ID NO 14
<211> LENGTH: 191
<212> TYPE: PRT
<213> ORGANISM: Artificial Sequence
<220> FEATURE:
<223> OTHER INFORMATION: G120K-N99C (amino acid) Synthetic Constructs / Mutant Human Growth Hormone Antagonists

<400> SEQUENCE: 14

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 15
<211> LENGTH: 576
<212> TYPE: DNA
<213> ORGANISM: Artificial Sequence
<220> FEATURE:
<223> OTHER INFORMATION: G120K-T142C (DNA) Synthetic Constructs / Mutant Human Growth Hormone Antagonists

<400> SEQUENCE: 15

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 16

<211> LENGTH: 191
<212> TYPE: PRT
<213> ORGANISM: Artificial Sequence
<220> FEATURE:
<223> OTHER INFORMATION: G120K-T142C (amino acid) Synthetic Constructs / Mutant Human Growth Hormone Antagonists

<400> SEQUENCE: 16

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 17
<211> LENGTH: 576
<212> TYPE: DNA
<213> ORGANISM: Artificial Sequence
<220> FEATURE:
<223> OTHER INFORMATION: G120K-H151C (amino acid) Synthetic Constructs / Mutant Human Growth Hormone Antagonists

<400> SEQUENCE: 17

```
ttcccaacca ttcccttatc caggcttttt gacaacgcta tgctccgcgc ccatcgtctg      60

caccagctgg cctttgacac ctaccaggag tttgaagaag cctatatccc aaaggaacag     120

aagtattcat tcctgcagaa cccccagacc tccctctgtt tctcagagtc tattccgaca     180

ccctccaaca gggaggaaac acaacagaaa tccaacctag agctgctccg catctccctg     240

ctgctcatcc agtcgtggct ggagcccgtg cagttcctca ggagtgtctt cgccaacagc     300

ctggtgtacg gcgcctctga cagcaacgtc tatgacctcc taaaggacct agaggaaaag     360

atccaaacgc tgatggggag gctggaagat ggcagccccc ggactgggca gatcttcaag     420

cagacctaca gcaagttcga cacaaactca tgcaacgatg acgcactact caagaactac     480

gggctgctct actgcttcag gaaggacatg gacaaggtcg agacattcct gcgcatcgtg     540

cagtgccgct ctgtggaggg cagctgtggc ttctag                               576
```

<210> SEQ ID NO 18
<211> LENGTH: 191

<212> TYPE: PRT
<213> ORGANISM: Artificial Sequence
<220> FEATURE:
<223> OTHER INFORMATION: G120K-H151C (amino acid) Synthetic Constructs / Mutant Human Growth Hormone Antagonists

<400> SEQUENCE: 18

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 19
<211> LENGTH: 576
<212> TYPE: DNA
<213> ORGANISM: Artificial Sequence
<220> FEATURE:
<223> OTHER INFORMATION: G120K-N99C-dPEGX-H151C (DNA) Synthetic Constructs / Mutant Human Growth Hormone Antagonists

<400> SEQUENCE: 19

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagacctaca gcaagttcga cacaaactca tgcaacgatg acgcactact caagaactac    480

gggctgctct actgcttcag gaaggacatg gacaaggtcg agacattcct gcgcatcgtg    540

cagtgccgct ctgtggaggg cagctgtggc ttctag                               576
```

<210> SEQ ID NO 20
<211> LENGTH: 191
<212> TYPE: PRT

<213> ORGANISM: Artificial Sequence
<220> FEATURE:
<223> OTHER INFORMATION: G120K-N99C-dPEGX-H151C (amino acid) Synthetic Constructs / Mutant Human Growth Hormone Antagonists

<400> SEQUENCE: 20

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 21
<211> LENGTH: 576
<212> TYPE: DNA
<213> ORGANISM: Artificial Sequence
<220> FEATURE:
<223> OTHER INFORMATION: G120K-T142C-dPEGX-N99C (DNA) Synthetic Constructs / Mutant Human Growth Hormone Antagonists

<400> SEQUENCE: 21

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 22
<211> LENGTH: 191
<212> TYPE: PRT
<213> ORGANISM: Artificial Sequence
<220> FEATURE:
<223> OTHER INFORMATION: G120K-T142C-dPEGX-N99C (amino acid) Synthetic Constructs / Mutant Human Growth Hormone Antagonists

<400> SEQUENCE: 22

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 23
<211> LENGTH: 576
<212> TYPE: DNA
<213> ORGANISM: Artificial Sequence
<220> FEATURE:
<223> OTHER INFORMATION: G120K-T142C-dPEGX-H151C (DNA) Synthetic Constructs / Mutant Human Growth Hormone Antagonists

<400> SEQUENCE: 23

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca tgcaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 24
<211> LENGTH: 191
<212> TYPE: PRT
<213> ORGANISM: Artificial Sequence
<220> FEATURE:

-continued

```
<223> OTHER INFORMATION: G120K-T142C-dPEGX-H151C (amino acid) Synthetic
      Constructs / Mutant Human Growth Hormone Antagonists

<400> SEQUENCE: 24

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```